US00PP15885P2

(12) United States Plant Patent
Deroose

(10) Patent No.: US PP15,885 P2
(45) Date of Patent: Jul. 19, 2005

(54) ***POGONATHERUM* PLANT NAMED 'DEPLABUN'**

(50) Latin Name: *Pogonatherum paniceum*
Varietal Denomination: Deplabun

(75) Inventor: Reginald Deroose, Evergem (BE)

(73) Assignees: NV Deroose Plants, Evergem (BE); Bunnik Plants B.V., Bleiswijk (NL)

( * ) Notice: Subject to any disclaimer, the term of this patent is extended or adjusted under 35 U.S.C. 154(b) by 0 days.

(21) Appl. No.: 10/766,772

(22) Filed: Jan. 28, 2004

(51) Int. Cl.[7] ..... A01H 5/00
(52) U.S. Cl. ..... Plt./384
(58) Field of Search ..... Plt./384

*Primary Examiner*—Anne Marie Grunberg
*Assistant Examiner*—June Hwu
(74) *Attorney, Agent, or Firm*—C. A. Whealy

(57) ABSTRACT

A new and distinct cultivar of *Pogonatherum* plant named 'Deplabun', characterized by its upright and mounted plant habit; freely branching, bushy and relatively vigorous growth habit; and green-colored leaf blades.

1 Drawing Sheet

Botanical classification/cultivar designation: *Pogonatherum paniceum* cultivar Deplabun.

BACKGROUND OF THE INVENTION

The present Invention relates to a new and distinct cultivar of *Pogonatherum* plant, botanically known as *Pogonatherum paniceum,* and hereinafter referred to by the name 'Deplabun'.

The new *Pogonatherum* was discovered by the Inventor in a controlled environment in Bleiswijk, The Netherlands in 2001, as a naturally-occurring whole plant mutation of *Pogonatherum paniceum* cultivar Compact, not patented. The new *Pogonatherum* was observed as a single flowering plant within a population of plants of the cultivar Compact. The selection of this plant was based on its plant size.

Asexual reproduction of the new *Pogonatherum* by tissue culture in a controlled environment in Evergem, Belgium since 2002 has shown that the unique features of this new *Pogonatherum* are stable and reproduced true to type in successive generations.

SUMMARY OF THE INVENTION

The cultivar 'Deplabun' has not been observed under all possible environmental conditions. The phenotype may vary somewhat with variations in environment such as temperature and light intensity, without, however, any variance in genotype.

The following traits have been repeatedly observed and are determined to be the unique characteristics of 'Deplabun'. These characteristics in combination distinguish 'Deplabun' as a new and distinct *Pogonatherum* cultivar:

1. Upright and mounded plant habit.
2. Freely branching, bushy and relatively vigorous growth habit.
3. Green-colored leaf blades.

Plants of the new *Pogonatherum* are most similar to plants of the parent cultivar Compact; however plants of the new *Pogonatherum* differ from plants of the cultivar Compact in the following characteristics:

1. Plants of the new *Pogonatherum* are not as compact as plants of the cultivar Compact.

2. Plants of the new *Pogonatherum* have longer internodes then plants of the cultivar Compact.
3. Plants of the new *Pogonatherum* have larger and lighter green-colored leaves than plants of the cultivar Compact.

Plants of the new *Pogonatherum* can be compared to plants of the *Pogonatherum* cultivar Monica, not patented. In side-by-side comparisons conducted in Evergem, Belgium, plants of the new *Pogonatherum* differed from plants of the cultivar Monica in the following characteristics:

1. Plants of the new *Pogonatherum* were stronger and bushier than plants of the cultivar Monica.
2. Plants of the new *Pogonatherum* had darker green-colored leaves than plants of the cultivar Monica.

BRIEF DESCRIPTION OF THE PHOTOGRAPH

The accompanying colored photograph illustrates the overall appearance of the new *Pogonatherum,* showing the colors as true as it is reasonably possible to obtain in colored reproductions of this type. Colors in the photograph may differ slightly from the color values cited in the detailed botanical description which accurately describe the colors of the new *Pogonatherum.* The photograph comprises a side perspective view of a typical plant of 'Deplabun' grown in a container.

DETAILED BOTANICAL DESCRIPTION

In the following description, color references are made to The Royal Horticultural Society Colour Chart, 2001 Edition, except where general terms of ordinary dictionary significance are used. The aforementioned photograph and following observations and measurements described plants grown in Bleiswijk, The Netherlands, under commercial practice during the summer in a glass-covered greenhouse. During the production of the plants, day temperatures were about 20° C. and night temperatures were about 18° C. Plants were grown with one plant per 12-cm container. Plants were about 15 weeks old when the photograph and description were taken.

Botanical classification: *Pogonatherum paniceum* cultivar Deplabun.

Parentage: Naturally-occurring whole plant mutation of *Pogonatherum paniceum* cultivar Compact, not patented.

Propagation:

*Type.*—By tissue culture.

*Time to initiate roots on a tissue-cultured cutting.*—Summer: About seven days at 20° C. Winter: About ten days at 20° C.

*Time to produce a fully-rooted tissue-cultured plantlet.*—Summer: About six weeks at 20° C. Winter: About seven weeks at 20° C.

*Root description.*—Fine, dense and freely branching; rhizomatous; 164C to 164D in color.

Plant description:

*Plant form.*—Upright plant habit; mounded inverted triangle to flattened globular form; freely basally branching, bushy and relatively vigorous growth habit.

*Plant height.*—About 19 cm.

*Plant width.*—About 29 cm.

*Stem description.*—Arrangement/quantity: Basally branching; about 150 basal branches per plant. Length: About 11.9 cm. Diameter: About 1.2 mm. Internode description: Hollow. Internode length: About 1.4 cm. Texture: Smooth, glabrous; nodes, pubescent. Strength: Strong. Color: 137A; towards the apex, 144A to 144B; nodes, 165A; occasionally directly above the nodes, N186C.

*Leaves.*—Arrangement: Two-ranked; sheathed. Blade length: About 2.5 cm. Blade width: About 7 mm. Sheath length: About 1.4 cm. Sheath width: About 7 mm. Shape: Narrowly lanceolate. Auricles: None observed. Apex: Acute. Margin: Entire. Texture, upper and lower surfaces: Glabrous, smooth; margins on sheaths sparsely pubescent. Venation pattern: Parallel. Color, leaf blade and sheath: Developing blades and sheaths, upper surface: 143A. Developing blades and sheaths, lower surface: 137C. Fully expanded blades and sheaths, upper surface: 137A. Fully expanded blades and sheaths, lower surface: 137B. Venation, upper surface: 137A. Venation, lower surface: 137B.

Flower description:

*Flowering habit.*—Minute inconspicuous single flowers arranged in terminal spikes. Usually about 90 flowers per spike. Flowers positioned upright. Flowers not fragrant.

*Natural flowering season.*—Plants typically flower during the spring and summer in The Netherlands. Flowering continuous during this period. Flowers not persistent.

*Inflorescence length.*—About 1.7 cm.

*Inflorescence diameter.*—About 3 mm.

*Flowers.*—Diameter: About 0.8 mm. Depth (height): About 2 mm.

*Flower buds.*—Length: About 1.8 mm. Diameter: About 0.2 mm. Shape: Linear. Color: 143B.

*Lemma.*—Quantity per flower: Two. Shape: Linear. Apex: Acute. Margin: Entire. Length: About 5 mm. Texture: Smooth, glabrous. Color, upper and lower surfaces: 199C.

*Palea.*—Quantity per flower: Two. Length: About 2 mm. Width: About 0.8 mm. Texture: Densely pubescent. Color, upper and lower surfaces: 145D.

*Peduncles.*—Angle: Erect. Length: About 1.8 cm. Diameter: About 0.5 mm. Strength: Moderately strong. Texture: Smooth, glabrous. Color: 144A to 144B.

*Reproductive organs.*—Stamens: Quantity per flower: One. Anther shape: Reniform, narrow. Anther length: About 1 mm. Anther color: 150C to 150D. Pollen amount: Moderate. Pollen color: 150D to 1D. Pistils: Quantity per flower: One. Pistil length: About 1 mm. Stigma shape: Two-parted. Stigma color: 1D. Style length: About 0.1 mm. Style color: 1D. Ovary color: 160D.

*Seed/fruit.*—Seed and fruit production has not been observed as reproductive organs are not formed.

Disease/pest resistance: Plants of the new *Pogonatherum* have not been observed to be resistant to pathogens and pests common to *Pogonatherums*.

Temperature tolerance: Plants of the new *Pogonatherum* have been observed to tolerate temperatures from 5 to 35° C.

It is claimed:

1. A new and distinct cultivar of *Pogonatherum* plant named 'Deplabun', as illustrated and described.

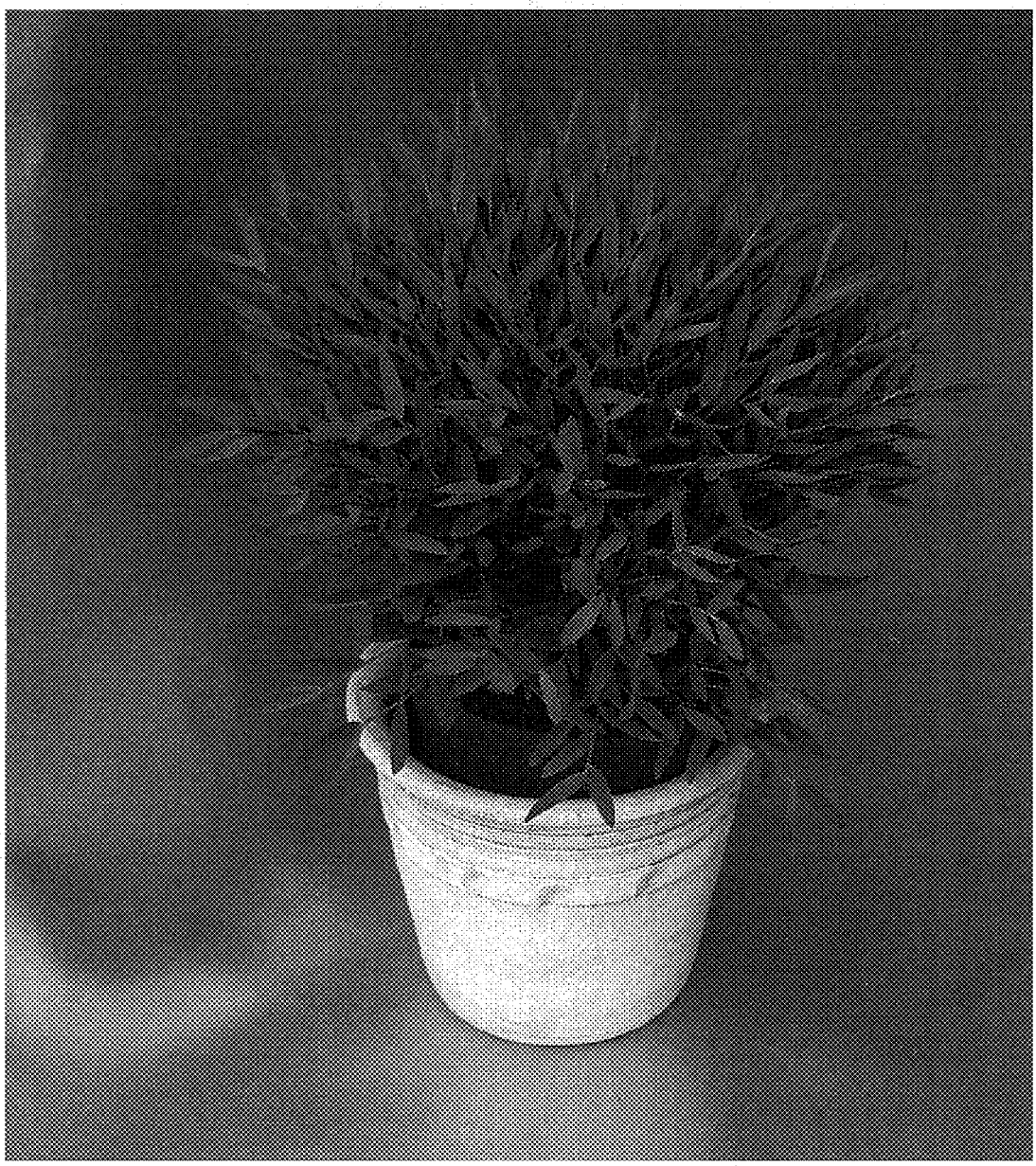

* * * * *